United States Patent [19]

Staats

[11] 4,117,337
[45] Sep. 26, 1978

[54] PATIENT POSITIONING INDICATION ARRANGEMENT FOR A COMPUTED TOMOGRAPHY SYSTEM

[75] Inventor: Peter Francis Staats, Waukesha, Wis.

[73] Assignee: General Electric Company, Milwaukee, Wis.

[21] Appl. No.: 848,275

[22] Filed: Nov. 3, 1977

[51] Int. Cl.² .............................................. G03B 41/16
[52] U.S. Cl. ................................. 250/445 T; 250/491
[58] Field of Search .................... 250/445 T, 490, 491

[56] References Cited

U.S. PATENT DOCUMENTS 3,708,663  1/1973  Buderman ........................... 250/491

Primary Examiner—Craig E. Church
Attorney, Agent, or Firm—Roger C. Turner

[57] ABSTRACT

A computed tomography system has an arrangement for indicating the staged position of a patient in relation to the location of a first scan by the system. The arrangement includes at least one energy beam source, such as a laser, which projects a visible pattern on the surface of the patient. The pattern corresponds to the central alignment of the system and to the location of the first scan of the system when a patient-supporting table is subsequently translated into a gantry of the system for x-ray examination. The pattern includes a central longitudinal line indicating a central longitudinal plane of the area to be scanned, and a transverse line indicating the location of the transverse plane of the first scan. The energy beam source of the arrangement is adjustable to project an angled line which corresponds to a tilted gantry or a tilted patient, or a tilted supporting table to indicate the location of the transverse plane of the first scan of the system. The patient is aligned and located in agreement to the projected patterns to thereby properly position the patient for the subsequent desired first scan by the system.

11 Claims, 4 Drawing Figures

PATIENT POSITIONING INDICATION ARRANGEMENT FOR A COMPUTED TOMOGRAPHY SYSTEM

BACKGROUND OF THE INVENTION

1. Field of the Invention

This invention relates generally to a system for performing computed x-ray tomography and more particularly to an arrangement for precisely indicating the proper staged position of a patient on a table prior to performing the tomography.

2. Description of the Prior Art

In one method of computed tomography a patient is supported for being translated along a longitudinal axis which is usually horizontally disposed. The axis coincides with the center of rotation of a rotatable gantry which has an x-ray source on one side of the center of rotation and a multiple array of x-ray detectors on the other side. A fan shaped x-ray beam that is thin in the longitudinal direction is projected through the patient as the gantry rotates so that the detectors may develop signals indicative of x-ray transmission characteristics along a plurality of paths through the patient undergoing examination. Analog signals representative of x-ray attenuation by all of the volume elements in a layer of the patient at various rotational angles are then converted to digital signals which are used by a computer to produce signals which may thereafter be used to produce a reconstructed image of the layer. The image is reconstructed by analyzing all of the signals within a central cross-sectional area of the system known as the "reconstruction circle". The analog signals are analyzed and converted based upon all of the x-ray attenuation taking place within the reconstruction circle. If the patient is improperly positioned so that a portion of the patient extends outside of the reconstruction circle, the attenuation of that portion will be erroneously interpreted. It is therefore important that the patient be properly aligned within the center of the reconstruction circle during the scan.

The x-ray beam is usually projected through a thin layer of the patient so that the reconstructed layer is essentially perpendicular to the longitudinal axis along which the patient is translated to obtain views of successive layers.

In the above described system, the patient is supported on a horizontal table which is translatable along a central longitudinal axis. The patient is positioned on the table and generally aligned for the first or reference scan. It is extremely important to determine the precise location of the first scan of the patient. By knowing the precise location of the first scan, the number of lead-in scans prior to the area of interest and lead-out scans following the area of interest can be eliminated and thereby maximize the utilization of the computed tomography system and minimize the radiation exposure to the patient. Knowledge of the reference scan is also required for analysis and correlation of the reconstructed images of the patient. As previously discussed, axial alignment is also necessary to facilitate centering of the patient within the image reconstruction circle of the system and also to facilitate analysis of images having symmetrical patterns.

One method of aligning and positioning a patient to a specific first scan involves the actual translation of the patient into the gantry prior to performing the scanning operation. Even with the help of internal light beams it is very difficult to observe the position of the patient relative to the geometry of the gantry and also difficult to reposition the patient while in the translated position. It is often necessary to retract the table for patient repositioning and then repeat the verification operation.

Another problem associated with patient positioning involves scans of which the gantry is tilted through a small vertical angle and is not perpendicular to the horizontal or longitudinal axis. On some occasions unique diagnostic information can only be obtained by viewing a slice or layer through the body which is taken at such a small vertical angle and is not perpendicular to the longitudinal axis along which the patient is translated. A tomography system having such a tiltable gantry is described in U.S. Pat. application Ser. No. 771,863 entitled GANTRY FOR COMPUTED TOMOGRAPHY filed in the name of Kelman et al and assigned to the same assignee as the present application. As the gantry is tilted either rearwardly (cranially) or forwardly (caudally), a reference line perpendicular to the top surface of the patient would not accurately display the reference scan.

Another problem associated with patient positioning involves a scan by a vertical gantry while the patient is tilted to a specific angle; particularly for neurological analysis of the head. One method of positioning the patient to the desired specific angle while on a horizontal table requires the use of a set of transparent protractor devices to be aligned with inscribed lines on the surface of the patient. These devices are time consuming, difficult to use and are not extremely accurate. Alternatively, the angular orientation can be accomplished by tilting the table through a small horizontal angle relative to the longitudinal axis of a vertical gantry. As the table is tiled, a reference line on the patient would not accurately display the horizontal alignment of the patient. Also, the horizontal translation of the angled table into the gantry may be less than when in the horizontal position and a reference line perpendicular to the top surface of the patient may not accurately display the reference scan.

Accordingly, one object of this invention is to provide an arrangement to indicate the position of the patient relative to the first scan of a gantry while the patient is in the staged position.

Another object of the present invention is to provide an arrangement to facilitate the alignment of a patient on a table while in the staged position of a computed tomography system.

Another object is to provide an arrangement for accurately indicating the plane of the first scan of a computed tomography system when the gantry of the system is tilted through a small vertical angle and is not perpendicular to the horizontal or longitudinal axis along which the patient is translated.

Still another object of this invention is to provide an arrangement for displaying a desired angle on the surface of a patient so that the patient can be easily and accurately positioned at that desired angle while in the staged position prior to translation into the gantry for scanning.

SUMMARY OF THE INVENTION

The invention is directed to an arrangement for indicating the staged position of a patient in relation to the first scan of a computer tomography system. The tomography system includes a source of an x-ray beam and a detector disposed on opposite sides about a generally vertical gantry. The terms x-ray and x-ray source are used herein for the sake of brevity and convenience but these terms should be construed as embracing gamma radiation and gamma sources and other penetrating radiation and sources as well. The gantry has a generally cylindrical opening for receiving the patient. The patient is supported on a generally horizontal table which is translatable along the longitudinal axis generally centered within the opening of the gantry. The table is displacable from an initial staged position outside of the gantry to a predetermined position within the gantry for the first scan of the patient. The table is further displacible for the purpose of disposing additional layers of the patient into the path of the x-ray beam.

The proper position of the patient on the table in the staged mode is indicated by energy beam sources which project visible patterns on the surface of the patient. The patterns correspond to the central alignment of the system and to the location of the first scan of the system when the patient supporting table is subsequently translated into the gantry. The first energy beam source is provided by a laser which projects a first pattern including a central longitudinal line indicating the vertical median plane of the area to be scanned, and a transverse line indicating the location of a central transverse axis of the first scan. A second energy source is provided by a laser which projects a second pattern including a longitudinal line indicating the central horizontal plane of the area to be scanned, and an adjustable generally vertical line indicating the location of the transverse plane of the first scan. The patient is located and aligned in agreement to the projected patterns to thereby properly position the patient for the subsequent desired first scan by the system.

BRIEF DESCRIPTION OF THE DRAWINGS

While the novel features of the invention are set forth with particularity in the appended claims, the invention will be better understood along with other features thereof from the following detailed description taken in conjunction with the drawings in which:

DESCRIPTION OF THE PREFERRED EMBODIMENT

Figure 1:
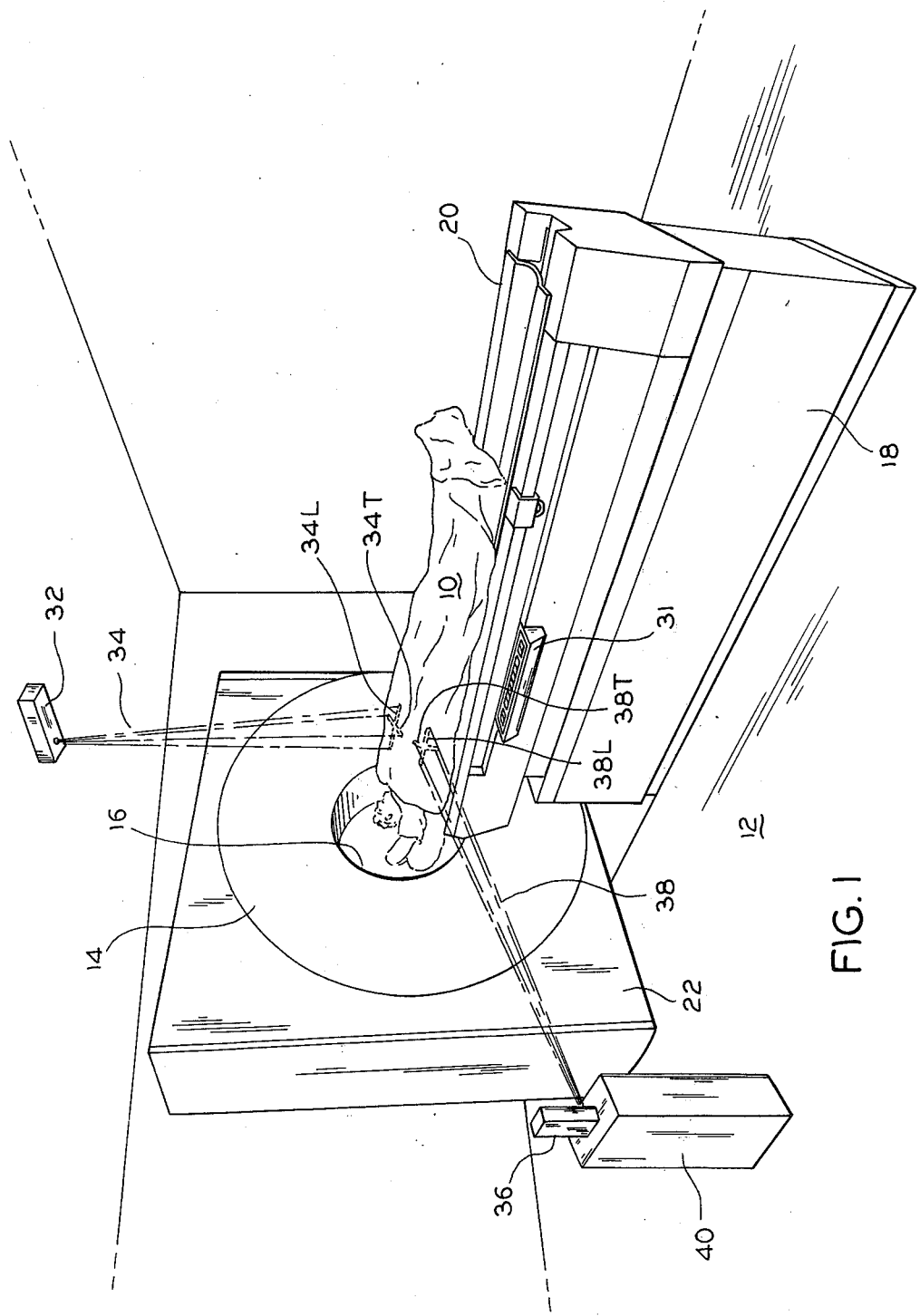
FIG. 1 is a perspective view of a patient in the staged position of a computed tomography system incorporating an arrangement for indicating the proper staged position of the patient.
Figure 2:
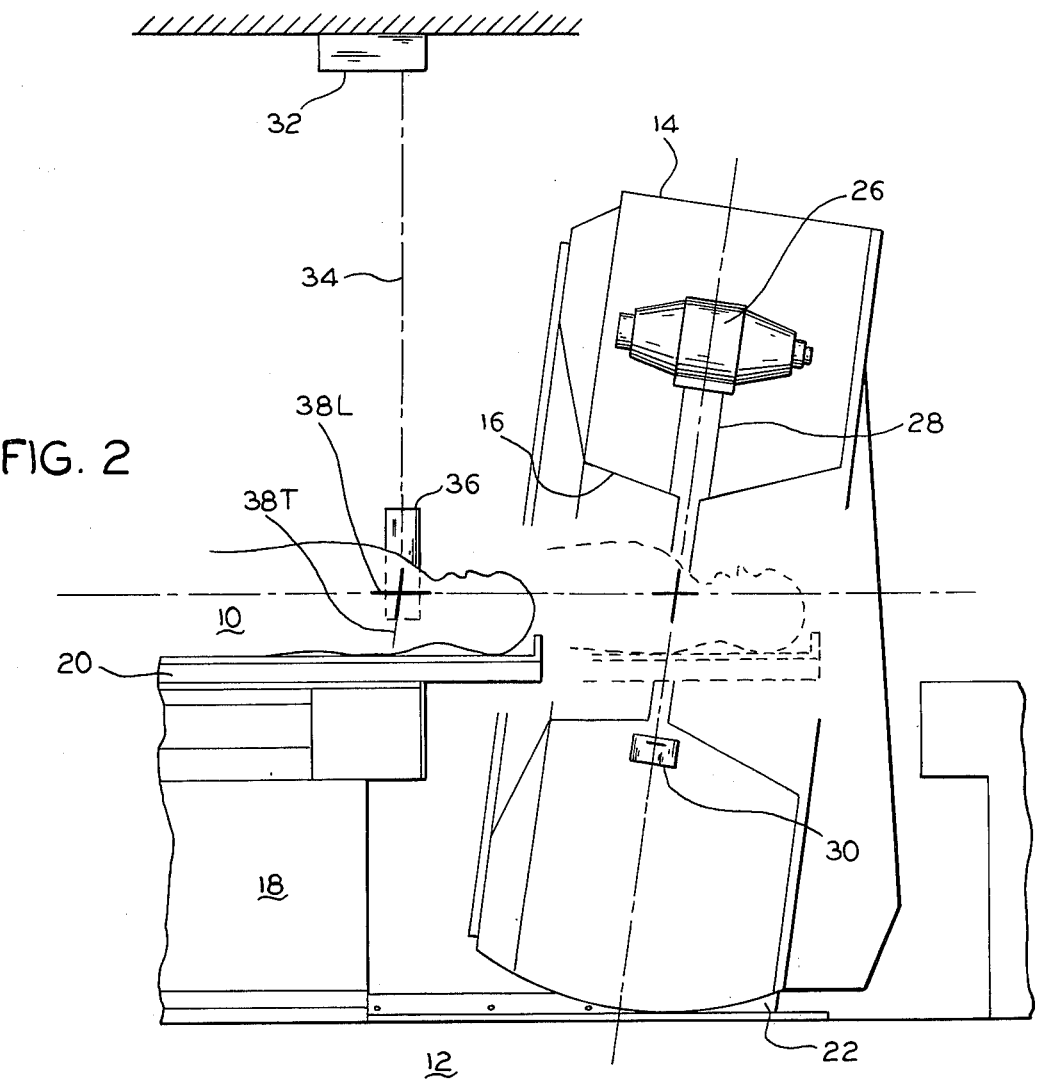
FIG. 2 is a right side partial sectional view of the computed tomography system showing the gantry in a tilted position, with the patient shown in the staged position and shown (in phantom) in position for the first scan.

Referring first to FIGS. 1 and 2 there is shown a patient 10 in the staged position of computed tomography system 12. X-ray scanning and obtaining x-ray attenuation data on a multitude of small volume elements of the patient 10 is carried out with components of a gantry which is generally designated by reference numeral 14. Gantry 14 is generally vertical having a cylindrical horizontal opening 16 for receiving patient 10 for examination. A table for supporting patient 10 is generally designated by reference numeral 18. Table 18 has a top 20 on which patient 10 may be supported in a recumbent position. Top 20 is adapted for being translated longitudinally so that it extends in cantilever fashion from table 18 for the purpose of disposing a first layer of patient 10 for scanning, then successive longitudinal translations for disposing additional layers of the patient into the path of the scanning x-ray beam.

Basic elements of the gantry 14 are shown in FIG. 2 sectional view. Gantry 14 is shown tilted rearwardly or cranially about a central transverse axis and is adapted in a commercial embodiment to be tiltable through angles of ±15° relative to vertical. Such a suitable gantry mechanism is described in greater detail in the above referenced copending application Serial No. 771,863. The gantry 14 includes a base 22 about which the components of the gantry can be tilted as previously described and rotated about a central longitudinal axis 24. An x-ray source 26 is mounted therein on one side of opening 16 and positioned so that the central ray of the x-ray beam emanating from the x-ray source passes through the longitudinal axis 24. Mounted to the output side of x-ray source 26 is a collimator device 28 which in this particular design collimates the x-ray beam into a thin fan shaped beam which originates from a substantially point source on the target of an x-ray tube in source 26. In a commercial embodiment, by way of example, the longitudinal thickness of the x-ray beam is about 1 cm and a slice or layer of corresponding thickness in the patient is penetrated by the beam for each scan. An x-ray detector and data acquisition assembly 30 is also mounted therein on the opposite side of opening 16 and is aligned with collimator 28. The detector portion has a curved x-ray input window behind which there is an array of adjacent detector cells, not visible, which each produce output signals corresponding with the intensity of the plurality of rays that radiate from the x-ray source and penetrate continuous series of volume elements of a patient layer that is disposed along the longitudinal axis during x-ray examination of the patient. A suitable detector is shown in a U.S. Patent No. 4,031,396 by Whetten et al., and assigned to the assignee of this application. Other detector forms are known to those skilled in the art. The discreet plurality of analog signals representative of x-ray attenuation by small volume elements in the patient are processed in a data acquisition system, after which the analog signals are converted to digital signals which are used by a computer, not shown, to execute the image reconstruction algorithm. The above described computed tomography system is generally known in the art.

Referring again to FIGS. 1 and 2 the position of patient 10 is shown relative to the gantry 14. Patient 10 is shown on table 18 with the head nearest the gantry. However, the patient can be positioned in either the head first or feet first orientation depending upon the area of the patient to undergo examination. Most lower chest and abdominal scans are performed with the feet of the patient first entering the gantry. Upper chest and neuro scans are performed with the head of the patient first entering the gantry. A mechanism (not shown) for advancing and retracting the patient 10 on tabletop 20 is included within the housing of table 18. Also included (not shown) within the housing of table 18 is a mechanism for raising and lowering the elevation of tabletop 20 and for making longitudinal and alignment adjustments of the tabletop to facilitate locating the patient in the proper staged position prior to advancing the tabletop into gantry 14 for the first scan. The adjustments of the tabletop 20 and operation of the system 12 are actuated by a control panel 31 located on the side of table 18. The translation distance from the staged position to the first scan position should be as short as possible while permitting convenient access to the patient in the staged position by the radiology technician. In this particular embodiment, the tabletop 20 is initially advanced 47 cm into the gantry for the first scan; therefore, the patient is aligned and positioned 47 cm forward of the gantry.

In order to precisely indicate the proper staged position of the patient relative to the first scan, alignment patterns are provided and are a principal feature of this invention.

A first energy beam source 32 is fixedly positioned vertically above the patient 10 on tabletop 20. The energy beam source 32 comprises a class II helium-neon gas laser having a beam splitter and lenses which project a cross-haired visible first pattern 34 on the upper surface of patient 10. The internal arrangement of components within the energy source 32 is not shown and not considered to be a part of this invention. Such an energy source is available from Gamex Inc. The laser of energy source 32 projects a red line pattern, visible under normal room lighting conditions, having a line thickness of approximately 5 mm when projected from a distance of 9 meters. Alternatively, the energy beam source could be provided by a conventional filiment lamp and could include a collimator or lenses to project a narrow energy beam pattern. The energy source 32 is fixedly attached to the ceiling of the examination room, or in other embodiments could be attached to a base or frame of the tomography system 12. Source 32 is positioned and precisely adjusted to project pattern 34 corresponding to the location of the first scan of the tomography system 12 when tabletop 20 is subsequently translated into gantry 14. First pattern 34 comprises a central longitudinal line 34L which indicates the vertical median plane of the scans of the system and coincides with the central longitudinal axis 24; and also, a transverse line 34T indicates the central transverse axis of the first scan of the system. When the gantry 14 is in the vertical non-tilted position, the transverse line 34T also accurately indicates the vertical plane of the first scan on the upper surface of patient 10.

Figure 3:
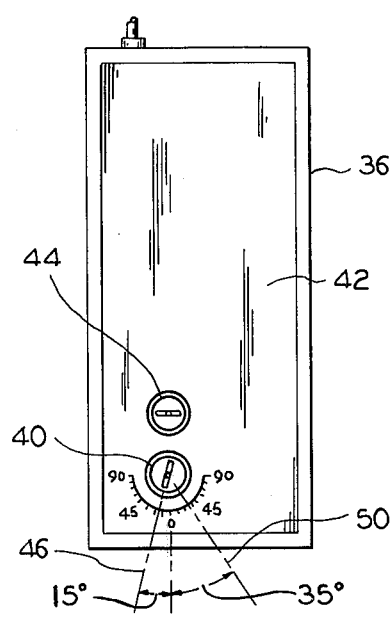
FIG. 3 is an enlarged front elevational view of the light source shown in FIG. 2.

A second energy beam source 36 is fixedly positioned horizontally and transversely to the longitudinal axis 24 and to the traverse of the patient supporting tabletop 20. The light source 36, similarly to the light source 32, comprises a class II helium-neon gas laser having a beam splitter and lenses which project a cross haired visible second pattern 38 on the side surface of patient 10. Energy source 36 is shown fixedly supported on a base 40, but in other embodiments could readily be attached to the side wall of the examination room or attached to a base or frame of the tomography system 12. Source 36 is positioned approximately 107 cm above the floor and is precisely adjusted to project a pattern 38 corresponding to the location of the center of the first scan of the tomography system 12, when tabletop 20 is subsequently translated into gantry 14. Second pattern 38 comprises a central longitudinal line 38L indicating the horizontal median plane of the scans of the system, and a generally vertical line 38T indicating the location of the transverse plane of the first scan of the system. As shown in FIG. 3 the lens projecting the generally vertical beam 38T from energy source 36 can be incrementally adjusted by the radiology technician by rotating an apertured knob 40 which rotates the lens. The cover 42 of source 36 is indexed concentric with knob 40 to indicate the vertical position as well as any angular rotation of the lens and resulting light pattern 38T emanating from source 36. Opening 44 over the lens projecting he horizontal line 38L remains constantly fixed in the horizontal orientation. Referring particularly to FIGS. 2 and 3 there are shown a patient 10 in the staged position for diagnostic examination requiring a tilted scan through the patient. For example, the gantry is tilted cranially 15°. The knob 40 is correspondingly rotated to the 15° indexed position 46 and thereby projects line 38T angled at 15° on the patient 10. The pattern 38T on the patient accurately indicates the location of the first scan by the tilted gantry 14 when the patient is subsequently translated into the gantry.

Before the patient is examined by the computed tomography system 12, a physician usually determines the area of interest to be examined in relation to a known reference point on the patient such as the sternal notch, xyphoid or the public bone. For exemplary purposes, the patient is referred for a series of scans of the left kidney. By a preliminary examination it was decided to scan areas from 6 cm to 10 cm below the xyphoid at 2½ cm increments for a total of 10 scans. The patient is assisted on the tabletop 22 with feet entering the gantry 14. The patient is generally positioned 47 cm outside of the gantry. The patient is measured with calipers at the scan area to determine the center elevation of the patient. If the patient is 18 cm thick the tabletop elevation is adjusted at the control panel 31 so that the second horizontal light pattern 38L is projected at 9 cm elevation on the side of the patient. The patient is next adjusted on the tabletop, or the tabletop is adjusted at the control panel, so that second transverse pattern 38T appears on the side of the patient 6 cm below the xyphoid. The patient is also aligned with the overhead projection of the first pattern 34 with the longitudinal center line of the patient corresponding with the central longitudinal pattern 34L. The patient is now in the proper staged position for the first scan.

Figure 4:
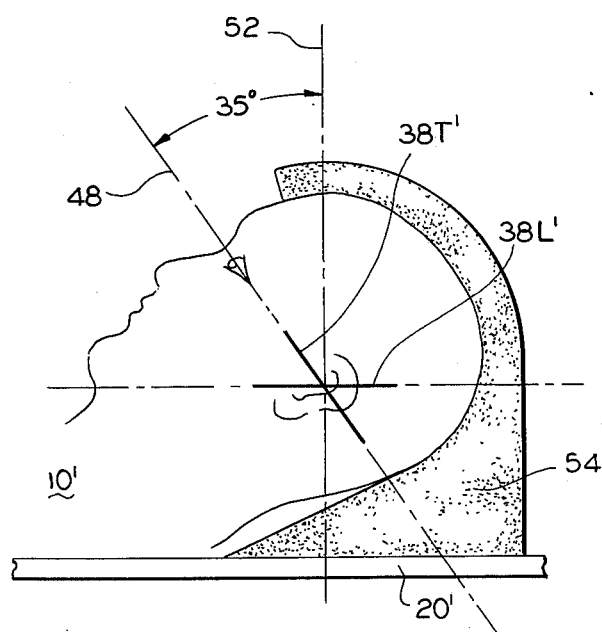
FIG. 4 is a side elevation view of a patient's head in which the arrangement of this invention is incorporated to indicate the desired angular position of the head for examination of the posterior fossa area.

The patient positioning indication arrangement is also particularly useful as shown in FIGS. 3 and 4 to facilitate positioning of the head for neuro scans. There are specific desired angles to position the head to produce unique diagnostic information, depending upon the physician's area of interest. A common reference line on a patient is the line between the eye and the ear known as the orbitomeatal line 48. Scan slices with the orbitomeatal line 20° off the vertical are often the routine plane for neuro scans. Scan slices parallel with the orbitomeatal line are used for facial and orbit examinations. Scan slices with the orbitomeatal line 35° off the vertical are used to examine the posterior fossa area.

For exemplary purposes, a physician is interested in seeing a patient's posterior fossa area. The patient 10' is located head toward the gantry 14 and with the orbitomeatal line 48 in a 35° angled position. The indicating pattern 38T' would be adjusted by knob 40 to the 35° indexed position 50 on energy source 36, caudally away from the gantry. The tabletop 20' is raised or lowered so that the patient is positioned with the central horizontal line 38L' is displayed on the external auditory canal. The patient should now have the horizontal line 38L' in the approximate center of the head through the external auditory canal and the generally vertical line 38T' should be along the orbitomeatal line 48. The generally vertical line 38T' is positioned 35° off the perpendicular scan plane 52. The head is secured in a head holding means 54 so that this angled line 38T' is reflecting on the orbitomeatal line. The patient should now be checked with the pattern from the overhead energy source 32 (not shown). The longitudinal line (34L — not shown) should be aligned with the median plane of the patient. The transverse axis line (34T — not shown) is also the scan plane of the system when the gantry is in the vertical position. In this example, the scan plane 52 would also go through the external auditory canal. When positioning the head into the gantry the patient is positioned with the most forward scan of interest being the first reference scan; since, in a particular commercial embodiment, the table increments out during the successive scans of the examination process. After confirming that the side patterns are still in position, the patient is in the proper staged position for translation into the gantry for performing the first scan. The translation and scanning operation is subsequently initiated at the operator's control panel 31.

The arrangement of this invention accurately indicates the position of the patient relative to the first or reference scan of the gantry while the patient is in the staged position. The arrangement also facilitates the alignment of the patient on the table while in the staged position. The adjustable feature of the side energy beam pattern accurately indicates the plane of the first scan of the system when the gantry of the system is tilted through a small vertical angle and is not perpendicular to the patient. The adjustable feature of the side energy beam pattern also facilitates alignment of the patient for neuro scans at specific angular planes relative to the orbitomeatal line of the patient.

While specific embodiments of the present invention have been illustrated and described herein it is realized that modifications and changes will occur to those skilled in the art. It is therefore to be understood that the appended claims are intended to cover all such modifications and changes as fall within the true spirit and scope of the invention.

What is claimed as new and desired to be secured by Letters Patent of the United States is:

1. An arrangement for indicating the staged position of a patient in relation to a first scan of a computed tomography system and for examining the patient with penetrating radiation such as x-rays, the arrangement including a source of an x-ray beam and a detector disposed about a generally vertical gantry having a generally cylindrical opening for receiving the patient, said system including a generally horizontal patient supporting table which is translatable along the longitudinal axis generally centered within the opening of the gantry wherein the table is displacable from an initial staged position outside of the gantry to a predetermined position within the gantry for the first scan of the patient and the table is further displaceable for the purpose of disposing additional layers of the patient into the path of the x-ray beam, said arrangement comprising a first energy beam source located so as to project a first visible pattern on the surface of the patient prior to the patient being translated into said gantry and said first pattern corresponding to the location of the first scan of said system when the patient-supporting table is subsequently translated into said gantry.

2. The arrangement as recited in claim 1 wherein said energy beam source comprises a laser.

3. The arrangement as recited in claim 1 wherein said energy beam source is fixedly positioned generally vertically above the patient for projecting said pattern.

4. The arrangement as recited in claim 3 wherein said pattern comprises a central longitudinal line indicating the vertical median plane of the area to be scanned, and a transverse line indicating the location of a central transverse axis of the first scan of the system.

5. The arrangement as recited in claim 1 wherein said energy beam source is fixedly positioned generally horizontally and transversly to the traverse of the patient-supporting table for projecting said pattern.

6. The arrangement as recited in claim 5 wherein said pattern comprises a central longitudinal line indicating the central horizontal plane of the area to be scanned, and a generally vertical line indicating the location of the transverse plane of the first scan.

7. The arrangement as recited in claim 6 wherein one of said gantry and said table is tiltable with respect to the other so as to provide scans at angles to the patient, and said energy beam source is adjustable so that said generally vertical line is angularly adjustable about a central transverse axis so as to indicate the location of the angular plane of said first scan on the patient, prior to the patient being translated into said gantry.

8. The arrangement as recited in claim 1 further comprising a second energy beam source for projecting a second visible pattern on the surface of the patient, said second pattern further defining the location of said first scan of said system when the patient — supporting table is subsequently translated into said gantry.

9. The arrangement as recited in claim 8 wherein said first energy beam source is fixedly positioned generally vertically above the patient for projecting said first pattern; and said second energy beam source is fixedly positioned generally horizontally and transversely to the traverse of the patient supporting table for projecting said second pattern.

10. The arrangement as recited in claim 2 wherein said first pattern comprises:
 (a) a central longitudinal line indicating the vertical median plane of the area to be scanned; and
 (b) a transverse line indicating the location of a central transverse axis of the first scan;
and wherein said second pattern comprises:
 (c) a longitudinal line indicating the central horizontal plane of the area to be scanned; and
 (d) a generally vertical line indicating the location of the transverse plane of the first scan.

11. The arrangement as recited in claim 9 wherein one of said gantry and said table is tiltable with respect to the other so as to provide scans at angles to the patient, and said second energy beam source is adjustable so that said generally vertical line is angularly adjustable about a central transverse axis so as to indicate the location of the angular plane of said first scan on the patient, prior to the patient being translated into said gantry.

* * * * *

UNITED STATES PATENT AND TRADEMARK OFFICE
CERTIFICATE OF CORRECTION

PATENT NO. :   4,117,337
DATED      :   September 26, 1978
INVENTOR(S) :  Peter Francis Staats It is certified that error appears in the above-identified patent and that said Letters Patent are hereby corrected as shown below:

column 8, line 44, "claim 2" should read -- claim 9 --.

Signed and Sealed this

Twenty-third Day of January 1979

[SEAL]

Attest:

RUTH C. MASON
Attesting Officer

DONALD W. BANNER
Commissioner of Patents and Trademarks